United States Patent [19]

Liebermann et al.

[11] Patent Number: 5,405,954
[45] Date of Patent: Apr. 11, 1995

[54] METAL PHTHALOCYANINES AND PROCESSES FOR THE PREPARATION THEREOF

[75] Inventors: George Liebermann, Mississauga; Roger E. Gaynor, Oakville; Ah-Mee Hor; Charles G. Allen, both of Mississauga, all of Canada

[73] Assignee: Xerox Corporation, Stamford, Conn.

[21] Appl. No.: 77,697

[22] Filed: Jun. 18, 1993

[51] Int. Cl.$^6$ .............................. C09B 67/12
[52] U.S. Cl. ................... 540/143; 540/139; 540/140
[58] Field of Search ................ 540/139, 140, 143

[56] References Cited

U.S. PATENT DOCUMENTS

| | | | |
|---|---|---|---|
| 3,657,272 | 4/1972 | Brach et al. | 260/314.5 |
| 3,985,767 | 10/1976 | Nicaise et al. | 540/143 |
| 4,471,039 | 9/1984 | Borsenberger et al. | 430/58 |
| 4,555,463 | 11/1985 | Hor et al. | 430/59 |
| 4,578,360 | 3/1986 | Regan et al. | 540/140 |
| 4,587,189 | 5/1986 | Hor et al. | 430/59 |
| 4,731,312 | 3/1988 | Kato et al. | 430/31 |
| 5,206,359 | 4/1991 | Mayo et al. | 540/143 |

FOREIGN PATENT DOCUMENTS 58-40798  9/1984  Japan .

OTHER PUBLICATIONS

Linsky et. al. Inorg. Chem., 1980, 19 pp. 3131–3135.
P. Mühl, "Kristall and Technik. Crystal research and technology." Dec. 17, 1966, pp. 432–435.
R. O. Louffy, et al. "Near-Infrared Photoreceptor Devices Incorporating Chloroindium Phthalocyanine", Journal of Imaging Science, vol. 29, No. 4, Jul./Aug. 1985, pp. 148–153.

*Primary Examiner*—John M. Ford
*Assistant Examiner*—Pavanaram K. Sripada
*Attorney, Agent, or Firm*—John L. Haack

[57] ABSTRACT

Disclosed is a process for the preparation of chloroindium phthalocyanine which comprises heating a mixture of indium trichloride and ortho-phthalodinitrile in a mixture of solvents comprised of a dialkylaminoalkanol and a high boiling second solvent; and cooling the mixture to enable precipitation.

30 Claims, No Drawings

METAL PHTHALOCYANINES AND PROCESSES FOR THE PREPARATION THEREOF

REFERENCE TO RELATED PATENTS

U.S. Pat. Nos. 5,100,752; 4,882,254; and 4,771,133 relate to phthalocyanine compositions and/or processes.

BACKGROUND OF THE INVENTION

This invention is generally directed to metal phthalocyanines and processes for the preparation thereof, and more specifically the present invention is directed to processes for obtaining halo, preferably chloroindium phthalocyanine, and layered photoconductive members comprised of the aforementioned phthalocyanine. In one embodiment, the present invention is directed to a process for the preparation of chloroindium phthalocyanines by initially heating a mixture of indium trichloride and a phthalodinitrile, such as ortho-phthalodinitrile in a mixture of solvents comprised of a dialkylaminoalkanol and a second high boiling solvent such as a chlorinated hydrocarbon; cooling the mixture to enable precipitation; and optionally separating the desired chloroindium phthalocyanine from the solution followed by an optional washing. The chloroindium phthalocyanine prepared by the processes of the present invention, can be selected as photogenerator materials or pigments in photoresponsive imaging members. The aforementioned photoresponsive imaging members may contain separate charge, especially hole transport layers such as arylamine hole transport molecules. The aforementioned photoresponsive imaging members can be negatively charged when the photogenerating layer is situated between the hole transport layer and the substrate, or positively charged when the hole transport layer is situated between the photogenerating layer and the supporting substrate. The layered photoconductor imaging members can be selected for a number of different known imaging and printing processes including, for example, electrophotographic imaging processes, especially xerographic imaging and other printing processes wherein negatively charged or positively charged images are rendered visible with toner compositions of the appropriate charge. Generally, the imaging members are sensitive in the wavelength regions of from about 700 to about 850 nanometers, thus diode lasers can be selected as the light source. Chloroindium phthalocyanines may also be selected as intense blue light-stable colorants for use in coatings, such as paint, inks, and as near infrared absorbing pigments suitable for use as IR laser optical recording materials.

Certain chloroindium phthalocyanine pigments are known, see for example, the α and β polymorphs, reference, for example, "Über die Polymorphie der Indium phthalocyanine" by P. Muhl, in *Kristall and Technik*, Vol. 2 page 431 to 435, Akademie-Verlag, 1967, D. Colaitis, in *Bull. Soc. Chim.*, page 23, 1962, and R. O. Loutfy et al., in *Journal of Imaging Science*, Vol. 29, No. 4, July/August, 1985, pp. 148 to 153. However, unlike some other phthalocyanines such as metal-free, copper, iron, and titanyl phthalocyanines, chloroindium phthalocyanines have had minimum general commercial use as pigments, or in electrophotographic or optical recording applications. In U.S. Pat. No. 4,555,463, there is illustrated a layered imaging member with a chloroindium phthalocyanine photogenerating layer, which chloroindium phthalocyanine may be prepared as described in *Inorganic Chemistry*, 1980, Vol. 19, pages 3131 to 3135, the disclosures of these references being totally incorporated by reference herein in their entirety. The use of photoreceptor devices incorporating chloroindium phthalocyanine is described in the aforementioned publication *Journal of Imaging Science*, Vol. 29, No. 4, July/August, 1985, pp. 148 to 153. Additionally, the utilization of chloroindium phthalocyanines or titanyl phthalocyanine in a multilayered electrographic device is illustrated in Japanese Patent Application Laid Open (Kokai) No. 59-166959. Other patents of interest which use chloroindium phthalocyanine and or derivatives for the preparation of photoconductive devices thereof include U.S. Pat. Nos. 4,587,189 and 4,471,039.

Several procedures for preparing haloindium phthalocyanines, such as chloroindium phthalocyanines are known. Some of the preparative methods result in phthalocyanines with halogen substituents on both the indium atom and the phthalocyanine ring. Such synthetic routes usually involve the reaction of o-phthalodinitrile with indium chloride in the absence of any solvents, such as described by G. P. Shaposhnikov, et al., in *Izv. Vyssh. Uchebn. Zaved., Khim. Techol.*, 20, pages 184 to 186, 1977. The same synthesis was used in Example I of U.S. Pat. No. 4,47 1,039 and Example I of U.S. Pat. No. 4,587,189. In both process situations, the reaction product was chloroindium chlorophthalocyanine, with partial ring chlorination (about 0.67 to 0.75 molecule of chlorine per phthalocyanine ring).

Synthetic methods which yield haloindium phthalocyanines with no ring halogenation for practical purposes, that is, within the limits of analytical methods for halogen, usually involve the use of a high boiling reaction solvent, such as quinoline, chloronaphthalenes, and the like. A typical synthesis is described by J. P. Linsky et al., in *Inorg. Chem.*, 19, 1980, page 3131 to 3135 and involves the reaction of o-phthalodinitrile with indium chloride in doubly distilled quinoline under reflux with a product yield of about 50%. A second typical synthesis involves the reaction of 1,3-diiminoisoindoline with indium chloride in quinoline, under reflux (at about 238° C.) for 6 hours with a yield of about 50%. This procedure also requires the synthesis of the precursor 1,3-diiminoisoindoline from o-phthalodinitrile, which increases the complexity and the cost of the process if a commercial implementation is contemplated.

U.S. Pat. No. 4,731,312 issued Mar. 5, 1988, to Kato discloses the preparation of electrophotographic members comprising certain indium phthalocyanines, XInPc where X is a halogen, as photoconductive materials in the charge carrier or generation layer. The reaction of o-phthalodinitrile and indium chloride in refluxing quinoline results in the formation of the desired chloride indium phthalocyanine. The product, however, is believed to be accompanied by other unidentified products or impurities considering the large variance observed in the reported empirical formula or ratio of elements. No yield or isolation details are provided. The chloroindium phthalocyanine used in the Japanese Patent Application Laid Open (Kokai) No. 59-166959, was synthesized by reacting o-phthalodinitrile and indium chloride in alpha-chloronaphthalene solvent at 250° C.

In the aforementioned documents, synthesis and processing conditions were disclosed for the preparation of the chloroindium phthalocyanine pigments which lead to relatively low reaction yields of up to about 50%, and to pigments which need additional extensive purifications before the pigments could be effectively used in certain electrophotographic applications.

To obtain a chloroindium phthalocyanine (ClInPc) based photoreceptor having high sensitivity to near infrared light, it is believed necessary to control the purity and chemical structure of the pigment as well as to prepare the pigment in the correct crystal modification.

In view of a variety of potential applications of chloroindium phthalocyanine pigments there is a need for economically viable processes in which the pigments are obtained in high purity and acceptable yields. Synthesis yields of a minimum of 75% are generally targeted for large scale, economical processes in which readily available raw materials and solvents are selected. Disadvantages of the prior art processes for preparing chloroindium phthalocyanine compounds include: having to employ a stoichiometric excess of the indium chlorides; the product is frequently contaminated with undesirable by products, for example, metal free phthalocyanine; use of commercially difficult to source materials such as 1,3-diiminoisoindoline or high purity quinoline; and particularly the yields are typically about 50% or less and economically unattractive for larger scale (multi-kilo) production operations.

In the present application, there is disclosed, for example, in one embodiment a high yield, high purity, and economical process for the preparation of chloroindium phthalocyanine. This method is an improvement over the prior art in that, for example, in embodiments thereof, the process is not complex, is rapid, and uses commercially readily available raw materials and solvents. Both the yield and the quality of the pigments often depends on synthesis conditions, for example, the solvent selected for use in the reaction. The high yield of the present process, compared to the processes described in the prior art, is achieved in embodiments by a synergistic effect, that is, by the use of a mixture of at least two solvents which includes an alkylalkanolamine such as a dialkylaminoethanol. The process of the present invention in one embodiment involves heating a mixture of indium trichloride and ortho-phthalodinitrile in a mixture of solvents comprised of a dialkylaminoalkanol and a high boiling second solvent resulting in a yield that is greater than what one would obtain with either solvent separately or individually.

U.S. Pat. No. 3,657,272 issued Apr. 18, 1972, discloses a direct process for preparing metal-free phthalocyanine comprising the steps of mixing o-phthalodinitrile in an ammonia-saturated alkylalkanolamine solvent, seeding the mixture with a catalytic amount of X-form phthalocyanine, heating said mixture to reflux temperature and maintaining said temperature for about 20 to about 70 minutes, and filtering the hot reaction product formed thereby. The metal-free phthalocyanine process described U.S. Pat. No. 3,657,272 is unique because it affords a direct synthesis of metal-free phthalocyanine instead of the previous art which involved intermediate synthesis of sodium phthalocyanine or other metal phthalocyanines, followed by demetallization to metal-free phthalocyanine. Metal-free phthalocyanine could not be synthesized directly by methods used for metal phthalocyanines synthesis in meaningful yields. It is believed that the alkylalkanolamine as used in the '272 reference is an active solvent in the reaction, that is, the solvent is believed to be participating in the intermediate reaction steps which lead to the formation of the metal-free phthalocyanine product.

The disclosures of all the aforementioned publications, and patents are totally incorporated herein by reference.

SUMMARY OF THE INVENTION

It is a feature of the present invention to provide processes for the preparation of chloroindium phthalocyanines with many of the advantages illustrated herein.

It is yet another feature of the present invention to provide economically scalable processes for the preparation of chloroindium phthalocyanines.

Another feature of the present invention relates to the preparation of chloroindium phthalocyanine including polymorphs known as $\alpha$ and $\beta$ forms.

Further, another feature of the present invention relates to the preparation of photogenerating chloroindium phthalocyanines by the heating a mixture of indium trichloride and phthalodinitrile, that is ortha-phthalodinitrile or 1,2-dicyanobenzene, in a mixture of solvents comprised of a dialkylaminoalkanol and at least one high boiling second solvent, such as a halogenated hydrocarbon, followed by cooling the mixture to enable precipitation and separation of the desired chloroindium phthalocyanine.

Moreover, another feature of the present invention relates to the preparation of haloindium phthalocyanines with high purities, and the use thereof in electrophotographic processes.

Additionally, another feature of the present invention relates to the preparation of chloroindium phthalocyanine in economic and acceptable yields of, for example, exceeding about 75 percent in embodiments of the present invention, in which the higher yield, compared to the processes described in the prior art, is achieved by a synergistic effect with the use of a mixture of at least two solvents which includes a dialkylaminoalkanol or alkylaminoalkanol.

Yet another feature of the present invention is the provision of a high degree of preparative versatility in, for example, the amounts and kinds of solvents selected. The preparative processes of the present invention enables successful preparation of ClInPc even with modifications to the process, such as using minimal amounts of the dialkylaminoalkanol solvent and a variety of high boiling second solvents. A minimal amount of dialkylaminoalkanol solvent as defined and used herein means a molar ratio of alkanol solvent to o-phthalodinitrile reactant of at least about 1:1.

A further feature of the present invention resides in the provision of a process for the preparation of chloroindium phthalocyanine which comprises heating a mixture of indium trichloride and ortha-phthalodinitrile in a dialkylaminoalkanol solvent; cooling the mixture to enable precipitation; and separating the desired chloroindium phthalocyanine from the reaction mixture followed by an optional washing.

Another feature of the present invention resides in the provision of photoresponsive imaging members with a photogenerator layer comprised of chloroindium phthalocyanine pigment obtained by the processes illustrated herein.

DESCRIPTION OF THE PREFERRED EMBODIMENTS

These and other features of the present invention are accomplished in embodiments thereof by the provision of certain phthalocyanines, processes for the preparation of halo, especially chloroindium phthalocyanines and photoresponsive imaging members thereof. More specifically, in one embodiment of the present invention there are provided processes for the preparation of chloroindium phthalocyanine (ClInPc) polymorphs, and particularly the β-polymorph of ClInPc, which comprise heating a mixture of indium trichloride and a phthalodinitrile like ortho-phthalodinitrile in a mixture of solvents comprised of a dialkylaminoalkanol and high boiling second solvent, such as a halogenated hydrocarbon; cooling the mixture to enable precipitation; and separating the desired chloroindium phthalocyanine from the solution followed by an optional washing. The product can be identified by various known means including elemental analysis, UV-Vis spectra, infrared spectra and X-ray powder diffraction (XRPD). The FTIR spectra of the chloroindium phthalocyanine pigment of the present invention in Nujol shows characteristics of the β form described by P. Muhl, in *Kristall and Technik*, Vol. 2 page 431–435, Akademie-Verlag, 1967, specifically the absence of absorption peaks at 903, 1050 and 1255 $cm^{-1}$ and the presence of an absorption peak at 781 $cm^{-1}$. The XRPD of the pigment is characterized by the strongest peak at the Bragg angle 2 theta (in degrees) of about 7.3, with additional main peaks at about 12.5, 13.1, 16.6, 18.2, 21.3, 22.1, 23.2, 24.7, 25.2, 26.5, 27.7, 28.2, 29.8, and 31.4. While these are the most predominant diffraction peaks for β chloroindium phthalocyanine, additional smaller peaks can be also identified.

Another embodiment of the present invention is directed to processes for the preparation of chloroindium phthalocyanines, which comprise heating a mixture of indium trichloride and ortha-phthalodinitrile in a mixture of solvents comprised of dimethylaminoethanol and chloronaphthalene; cooling the mixture to enable precipitation; and separating the desired chloroindium phthalocyanine from the solution followed by an optional washing.

In embodiments, heating a mixture of indium trichloride and ortho-phthalodinitrile in a mixture of solvents is accomplished at from about 125° C. to about 250° C. during a period of from about 0.5 hours to about 10 hours.

The aforementioned reactants that can be selected in effective amounts of, for example, from about 1 weight percent to about 40 weight percent of the solvent mixture of dialkylaminoalkanol and a second high boiling solvent.

As the solvent mixture, there can be selected a dialkylaminoalkanol, such as dimethylaminoethanol, and a cosolvent, such as an halogenated hydrocarbon, such as chloronaphthalene or other halogenated hydrocarbons with from 1 to about 6 halogen atoms such as fluorobenzene, and bromobenzene which will effectively dissolve the reactants and the chloroindium phthalocyanine product in effective amounts of, for example, a ratio of from about 1 to 50 parts of dialkylaminoalkanol to about 50 parts of cosolvent such as 1-chloronaphthalene. In an embodiment of the present invention, a preferred solvent mixture is comprised of 1:7 weight ratio of a dialkylaminoalkanol and a halogenated hydrocarbon.

The indium trichloride to ortho-phthalodinitrile weight ratio is from about 1:4 to about 1:8 and preferably from 1:4 to 1:6. A stoichiometric ratio (1:4) or an excess of phthalodinitrile is preferred. The use of an excess of phthalodinitrile does not lead to the formation of a metal-free phthalocyanine byproduct as may be experienced with methods using other solvent systems. Excess of indium trichloride is preferably avoided as excess $InCl_3$ may lead to the formation of undesired chlorinated byproducts.

The dialkylaminoalkanol to ortho-phthalodinitrile molar ratio when the dialkylaminoalkanol is used alone or in combination with a cosolvent is at least about 1:1 to about 1:10, as the amount of dialkylaminoalkanol present has a substantial effect on the yield of the reaction.

The ortho-phthalodinitrile is dissolved in from about a 1:4 to about 1:20 weight ratio of the solvent, such as in a mixture of a dialkylaminoalkanol and a halogenated hydrocarbon. The use of a more concentrated reaction mixture could create mixing problems as the pigment is formed in the reaction, while a too dilute system is not desired for large scale processes and results in a low product throughput.

Cooling the reaction mixture containing the chloroindium phthalocyanine product to enable the separation of the pigment is accomplished by lowering the temperature of the mixture to about 90 to about 0° C., preferably to about 30° C. to about 10° C. over about 0.5 to 2 hours.

Separation of the product is readily accomplished by known methods, for example, filtration, centrifugation, and the like.

Optional washing is preferably accomplished by successively washing with organic and aqueous solvents, such as alcohols, ketones, formamides, pyrrolidones, water, dilute aqueous bases such as ammonium hydroxide, sodium hydroxide, and the like. A typical washing sequence comprises washing with a first alcohol, a second alcohol, a formamide, water and then a third alcohol. A preferred washing sequence leading to product with a purity of greater than 99.9% is accomplished by successively washing with solvents comprising methanol, isopropanol, dimethylformamide, water and then methanol as indicated herein.

The resulting chloroindium phthalocyanine obtained by filtration separation is dried by heating at a temperature of from about 70° C. to about 150° C., under vacuum or using an inert hot carrier gas such as nitrogen.

The alkylaminoalkanol solvent is selected, for example, from the group consisting of monoalkylaminoalkanols and dialkylaminoalkanols with the dialkylaminoalkanols as the preferred solvents. Typical dialkylaminoalkanols include dimethylaminoethanol, dimethylaminopropanol isomers, diethylaminoethanol, diethylaminopropanols, and the like. The high boiling second solvent, with a boiling point higher than the selected alkylaminoalkanol solvent, is selected from any suitable group of solvents, such as halogenated hydrocarbon solvents, especially chlorinated aromatic solvents, N-alkylpyrrolidones or other suitable solvents. Preferred halogenated hydrocarbon solvents are chloronaphthalenes, such as 1-chloronaphthalene, chlorobenzenes and chlorotoluenes which have from about 1 to about 6 chlorine atoms. Preferred N-alkylpyrrolidones include N-methyl pyrrolidone, N-ethylpyrrolidone and N-cyclohexylpyrrolidone. The identity and purity of the product was determined by IR and elemental analysis, respectively. The β or "beta" polymorphic form of the products were determined by XRPD analysis.

Typical small scale or pilot plant scale reactions were accomplished in embodiments of the present invention as follows: heating gram or kilogram quantities of a mixture of indium trichloride and ortha-phthalodinitrile in a mixture of solvents comprised of a dialkylaminoalkanol and high boiling second solvent; cooling the mixture to enable precipitation; and separating the desired chloroindium phthalocyanine by filtration followed by optional washing to isolate the pigment in yields greater than about 75 percent based upon the weight of the starting indium trichloride.

The use of specific mixtures of a dialkylaminoalkanol and a high boiling second solvent such as a halogenated hydrocarbon, in particular, preferably dimethylaminoethanol and chloronaphthalene, in the synthesis of chloroindium phthalocyanine from stoichiometric (mole ratio 1:4) or approximately stoichiometric equivalents of indium trichloride and o-phthalodinitrile provides significantly improved yields over those yields which can be obtained using a single solvent as described herein and disclosed in the aforementioned prior art processes.

The metal containing phthalocyanine compounds prepared by processes of the present invention possess high purities and perform in electrographic applications and devices comparable to other metal phthalocyanine compounds disclosed in the prior art.

Numerous different layered photoresponsive imaging members with the phthalocyanine pigments obtained by the processes of the present invention can be fabricated. In one embodiment, the layered photoresponsive imaging members are comprised of a supporting substrate, a charge transport layer, especially an aryl amine hole transport layer, and situated therebetween, a photogenerator layer comprised of chloroindium phthalocyanine obtained with the processes of the present invention. Another embodiment of the present invention is directed to positively charged layered photoresponsive imaging members comprised of a supporting substrate, a charge transport layer, especially an aryl amine hole transport layer, and as a top overcoating, a layer containing chloroindium phthalocyanine pigments obtained with the processes of the present invention. There is provided in accordance with the present invention an improved negatively charged photoresponsive imaging member comprised of a supporting substrate, a thin adhesive layer, a photogenerator layer containing a chloroindium phthalocyanine, obtained by the processes of the present invention, applied by vacuum deposition, and as a top layer aryl amine hole transporting molecules dispersed in a polymeric resinous binder. Moreover, there is provided in accordance with the present invention an improved negatively charged photoresponsive imaging member comprised of a supporting substrate, a thin adhesive layer, a photogenerator layer containing a chloroindium phthalocyanine, obtained by the processes of the present invention, dispersed in a polymeric resinous binder, and as a top layer, aryl amine hole transporting molecules dispersed in a polymeric resinous binder.

The photoresponsive imaging members of the present invention can be prepared by a number of known methods, the process parameters and the order of coating of the layers being dependent on the member desired. The imaging members suitable for positive charging can be prepared by reversing the order of deposition of photogenerator and hole transport layers. The photogenerating and charge transport layers of the imaging members can be coated as solutions or dispersions onto selective substrates by the use of a spray coater, dip coater, extrusion coater, roller coater, wire bar coater, slot coater, doctor blade coater, gravure coater, and the like, and dried at from 40 to about 200° C. for from 10 minutes to several hours under stationary conditions or in an air flow. The coating is carried out in such a manner that the final coating thickness is from 0.01 to about 30 microns after it has dried. The fabrication conditions for a given layer will be tailored to achieve optimum performance and cost in the final device. The photogenerating layer can be also applied onto selected substrates by other methods, such as vacuum deposition or powder coating.

Imaging members containing chloroindium phthalocyanine pigments of the present invention are useful in various electrostatographic imaging and printing systems, particularly those conventionally known as xerographic processes. Specifically, the imaging members of the present invention are useful in xerographic imaging processes wherein the chloroindium phthalocyanines pigments absorb light of a wavelength of from about 600 nanometers to about 900 nanometers. In these known imaging processes, electrostatic latent images are initially formed on the imaging member followed by development, and thereafter transferring the image to a suitable substrate.

Moreover, the imaging members of the present invention can be selected for electronic printing processes with gallium arsenide light emitting diode (LED) arrays or diode lasers which typically function at wavelengths of from 660 to about 830 nanometers.

Substrate layers selected for the imaging members of the present invention can be opaque or substantially transparent, and may comprise any suitable material having the requisite mechanical properties. Thus, the substrate may comprise a layer of insulating material including inorganic or organic polymeric materials, including polycarbonates, polyamides, polyurethanes, polyesters such as MYLAR ® a commercially available polymer from DuPont, and the like. If desired, a semiconductive or conductive substrate can be coated onto the insulating material, such as a semiconductive surface layer of indium tin oxide, or a conductive material inclusive of aluminum titanium, zirconium, chromium, nickel, and the like. In addition, the substrate can comprise a metallized plastic, such as titanized or aluminized MYLAR ®, wherein the metallized surface is in contact with the photogenerating layer or any other layer situated between the substrate and the photogenerating layer. The coated or uncoated substrate may be flexible, seamless, or rigid and may have a number of many different configurations, such as for example a plate, a cylindrical drum, a scroll, a seamed loop belt, a seamless flexible belt, an endless flexible belt, and the like. In some situations, it may be desirable to coat on the back of the substrate, particularly when the substrate is a flexible organic polymeric material, with an anticurl layer, such as for example polycarbonate materials commercially available as MAKROLON ®.

The thickness of the substrate layer depends on many factors, including economical considerations, thus this layer may be of substantial thickness, for example, over 3,000 microns; or of minimum thickness providing there are no adverse effects on the system. In one embodiment, the thickness of this layer is from about 75 microns to about 300 microns.

The photoconductive imaging member may optionally contain a charge blocking layer situated between the conductive substrate and the photogenerating layer. This layer may comprise metal oxides, such as aluminum oxide and the like, or materials such as silanes and polyesters. Additional examples of suitable materials include polyisobutyl methacrylate, copolymers of styrene and acrylates such as styrene/n-butyl methacrylate, copolymers of styrene and vinyl toluene, polycarbonates, alkyl substituted polystyrenes, styrene-olefin copolymers, polyesters, polyurethanes, polyterpenes, silicone elastomers, mixtures thereof, copolymers thereof, and the like. The primary purpose of this layer is to prevent charge injection from the substrate during and after charging.

Intermediate adhesive layers between the substrate and subsequently applied layers may be desirable to improve adhesion. Typical adhesive layers include film forming polymers such as polyester, polyvinylbutyral, polyvinylpyrrolidone, polycarbonate, polyurethane, polymethyl methacrylate, and the like, and mixtures thereof. Since the surface of the substrate can be a metal oxide layer or an adhesive layer, the expression "substrate" as employed herein is intended to include in embodiments a metal oxide layer with or without an adhesive layer on a metal oxide layer.

In addition, the photoconductive imaging member may also optionally contain an adhesive interface layer situated between the hole blocking layer and the photogenerating layer. This layer may comprise a polymeric material such as polyester, polyvinyl butyral, polyvinyl pyrrolidone, and the like.

With further regard to the imaging members, the photogenerator layer is preferably comprised of the chloroindium phthalocyanine pigments obtained with the processes of the present invention. Generally, the thickness of the photogenerator layer depends upon a number of factors, including the method of coating or deposition, the amount of binder resin used, the thicknesses of the other layers and the amount of photogenerator material contained in this layer. Accordingly, this layer can be of a thickness of from about 0.05 micron to about 10 microns when the chloroindium phthalocyanine photogenerator composition is present in an amount of from about 5 percent to about 100 percent by volume. In one embodiment, this layer is of a thickness of from about 0.25 micron to about 1 micron, when the photogenerator composition is present in this layer in an amount of 30 to 100 percent by volume. The maximum thickness of this layer in an embodiment is dependent primarily upon factors, such as photosensitivity, electrical properties and mechanical considerations. The charge generator layer can be obtained by dispersion coating the chloroindium phthalocyanine obtained with the processes of the present invention, and a binder resin with a suitable solvent. The binder may be optionally omitted. The dispersion can be prepared by mixing and/or milling the chloroindium phthalocyanine in equipment such as paint shakers, ball mills, sand mills and attritors. Common grinding media such as glass beads, steel balls or ceramic beads may be used in this equipment. Illustrative examples of polymeric binder resinous materials that can be selected for the photogenerator pigment include those polymers as disclosed in U.S. Pat. No. 3,121,006, the disclosure of which is totally incorporated herein by reference. The binder resin may be selected from a wide number of polymers such as poly(vinyl butyral), poly(vinyl carbazole), polyesters, polycarbonates, poly(vinyl chloride), polyacrylates and methacrylates, copolymers of vinyl chloride and vinyl acetate, phenoxy resins, polyurethanes, poly(vinyl alcohol), polyacrylonitrile, polystyrene, and the like. The solvents used to dissolve these binders depend upon the particular resin. In embodiments of the present invention, it is desirable to select solvents that do not effect the other coated layers of the device. Examples of solvents useful for coating chloroindium phthalocyanine dispersions to form a photogenerator layer are ketones, alcohols, aromatic hydrocarbons, halogenated aliphatic hydrocarbons, ethers, amines, amides, esters, and the like. Specific examples are cyclohexanone, acetone, methyl ethyl ketone, methanol, ethanol, butanol, amyl alcohol, toluene, xylene, chlorobenzene, carbon tetrachloride, chloroform, methylene chloride, trichloroethylene, tetrahydrofuran, dioxane, diethyl ether, dimethylformamide, dimethylacetamide, butyl acetate, ethyl acetate and methoxyethyl acetate, and the like, and mixtures thereof.

Coating of the chloroindium phthalocyanine dispersion in embodiments of the present invention can be accomplished with spray, dip, wire bar, slide and slot coating methods such that the final dry thickness of the charge generator layer is from 0.01 to 30 microns and preferably from 0.1 to 15 microns after being dried at 40 to 150° C. for 5 to 90 minutes.

The chloroindium phthalocyanine photogenerator material can be applied by evaporation methods, such as by vacuum coating as described in U.S. Pat. No. 4,555,463.

The charge transport layer is a substantially non-photoconductive material which supports the injection of photogenerated holes from the generator layer. The hole transporting layer is generally of a thickness of from about 5 microns to about 75 microns, and preferably of a thickness of from about 10 microns to about 40 microns. The charge transport layer may be a material comprising a hole transporting small molecule in an inactive binder, or a charge transporting polymer such as an arylamine polycondensation polymer. Typical hole transporting small molecules are aryl amines including molecules of the following formula

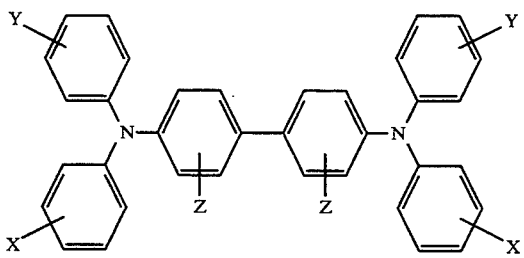

dispersed in a highly insulating and transparent organic resinous binder, wherein substituents X, Y, and Z are selected from the group consisting of alkyl, hydroxy, hydrogen or halogen, especially those substituents selected from the group consisting of (ortho) $CH_3$, (para) $CH_3$, (ortho) Cl, (meta) Cl, (para) Cl, (ortho) OH, (meta) OH and (para) OH.

Examples of specific aryl amines are N,N'-diphenyl-N,N'-bis(alkylphenyl)-1,1-biphenyl-4,4'-diamine wherein alkyl is selected from the group consisting of methyl, such as 2-methyl, 3-methyl and 4-methyl, ethyl, propyl, butyl, hexyl, and the like. With chloro substitution, the amine is N,N'-diphenyl-N,N'-bis(halo phenyl)-1,1'-biphenyl-4,4'-diamine wherein halo is 2-chloro, 3-chloro or 4-chloro. Other known hole transporting compounds can be selected.

Examples of the highly insulating and transparent resinous material or inactive binder resinous material for the transport layers include materials such as those described in U.S. Pat. No. 3,121,006. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binders are comprised of polycarbonate resins having a molecular weight of from about 20,000 to about 100,000 with a molecular weight of from about 50,000 to about 100,000 being particularly preferred. Generally, the resinous binder contains from about 10 to about 75 percent by weight of the active material corresponding to the foregoing formula, and preferably from about 35 percent to about 50 percent of this material.

Examples of hole transporting polymers are arylamine poly(carbonates), poly(ethercarbonates) and polyesters described in U.S. patents 4,801,517, 4,806,443, 4,806,444 and 5,028,687.

Also, included within the scope of the present invention are methods of imaging and printing with the photoresponsive devices illustrated herein. These methods generally involve the formation of an electrostatic latent image on the imaging member, followed by developing the image with a toner composition, reference U.S. Pat. Nos. 4,560,635; 4,298,697 and 4,338,390, subsequently transferring the image to a suitable substrate, and permanently affixing the image thereto. In those environments wherein the device is to be used in a printing mode, the imaging method involves the same steps with the exception that the exposure step can be accomplished with a laser device or image bar.

The invention will now be described in detail with reference to specific preferred embodiments thereof, it being understood that these examples are intended to be illustrative only. The invention is not intended to be limited to the materials, conditions, or process parameters recited herein, it being noted that all parts and percentages are by weight unless otherwise indicated. Comparative examples are included.

EXAMPLE I

Synthesis of Chloroindium Phthalocyanine using Dimethylaminoethanol as Reaction Solvent.

Ortho-phthalodinitrile (64.0 grams) was added to 320 grams of dimethylaminoethanol in a 1,000 mL, three necked round bottom flask. Anhydrous indium trichloride (22.1 grams) was added under agitation. The reaction mixture was heated to 138° to 139° C. and the reaction continued for 3 hours under a slight reflux. After cooling to about 25° C. for about 30 minutes under a nitrogen atmosphere, to precipitate the crude product pigment which was filtered with vacuum filtration using a Buchner funnel. The resulting wet cake was washed in the funnel with 350 grams methanol and then reslurried and washed with 300 grams isopropanol (four times at room temperature), 300 grams dimethylformamide (eight times at 70° C.), 300 grams deionized water (four times at 70° C.), and 300 grams of methanol (two times at room temperature) and dried. The desired chloroindium phthalocyanine product was isolated as 36.3 grams of a blue pigment, in 52 percent yield based on the starting indium chloride. The UV-Vis spectra of a dilute solution of the product pigment in chloronaphthalene confirmed that the desired product was obtained and confirmed that no metal free phthalocyanine was present.

The elemental analysis of the product was: Calcd for $C_{32}H_{16}N_8InCl$: C,57.94; H, 2.42; N, 16.91; In, 17.36; and Cl, 5.35. Found: C, 58.28; H,2.36; N, 16.78; In, 17.46; and Cl, 5.23; and a duplicate: C, 57.32; H, 2.58; N, 16.95; In, N.D.; and Cl, 5.42.

EXAMPLE II

Synthesis of Chloroindium Phthalocyanine using a mixture of Dimethylaminoethanol and Chloronaphthalene as Reaction Solvent.

Ortho-phthalodinitrile (64.0 grams) was added to 320 grams of chloronaphthalene and 44.57 grams dimethylaminoethanol in a 1,000 mL three necked round bottom flask. Anhydrous indium trichloride (22.1 grams) was added under agitation. The reaction mixture was heated to 130 to 140° C., maintained for one hour at this temperature, then the reaction temperature was increased to 165° to 170° C. and the reaction continued for an additional two hours. After cooling to about 25° C. for 30 minutes under nitrogen atmosphere, the pigment was filtered, using vacuum filtration with a Buchner funnel. The wet cake was washed in the funnel with 350 grams methanol and then reslurried and washed with 300 grams isopropanol (four times at room temperature), 300 grams dimethylformamide (four times at 70° C.), 300 grams deionized water (four times at 70° C.), and 300 grams of methanol (two times at room temperature) and dried. The desired chloroindium phthalocyanine product was isolated as 54 grams of a blue pigment, in 81.5 percent yield based on the starting indium chloride. The UV-Vis spectra of a dilute solution of the pigment in chloronaphthalene confirmed that the desired product was obtained and confirmed that no metal free phthalocyanine was present.

The elemental analysis of the product was: Calcd for as in Example I: C,57.99; H, 2.43; N, 16.91; In, 17.32; and Cl, 5.35. Found:C, 57.93; H, 2.64; N, 16.9; In, N.D.; and Cl, 5.41.

The synthesis of chloroindium phthalocyanine using the mixture of dimethylaminoethanol and chloronaphthalene as the reaction solvent was repeated using the same molar ratio of ortho-phthalodinitrile to dimethylaminoethanol molar ratio of 1:1 with a yield of 85.0 percent. When the molar ratio of ortho-phthalodinitrile to dimethylaminoethanol was reduced to 1:0.5 a yield of 60.4 percent was obtained. When the molar ratio of ortho-phthalodinitrile to dimethylaminoethanol was reduced to 1:0.25 a yield of 25.7 percent was obtained. Thus, the molar ratio of ortha-phthalodinitrile to dimethylaminoethanol is believed to be an important factor in obtaining high yields.

EXAMPLE III

Synthesis of Chloroindium Phthalocyanine using a mixture of Dimethylaminoethanol and N-Methylpyrrolidone as Reaction Solvent.

Ortho-phthalodinitrile (64.0 grams) was added to 320 grams of N-methylpyrrolidone and dimethylaminoethanol (44.57 grams) in a 1,000 mL three necked round bottom flask. Anhydrous indium trichloride (22.1 grams) was added under agitation. The reaction mixture was heated to 137° to 144° C., maintained for one hour at this temperature, then the reaction temperature was increased to 167° to 168° C. and the reaction continued for an additional one hour and forty five minutes. After cooling to about 40° C. under nitrogen atmosphere, the pigment was filtered, using vacuum filtration with a Buchner funnel. The wet cake was washed in the funnel with 350 grams methanol and then reslurried and washed with 300 grams isopropanol (four times at room temperature), 300 grams dimethylformamide (five times at 70° C.), 300 grams deionized water (three times at 70° C.), and 300 grams of methanol (two times at room temperature), and dried. The desired chloroindium phthalocyanine β-polymorph product was isolated as 40.07 grams of a blue pigment, in 60.5 percent yield based on the starting indium chloride. The UV-Vis spectra of a dilute solution of the pigment in chloronaphthalene confirmed that the desired product was obtained and confirmed that no metal free phthalocyanine was present.

The elemental analysis of the product was: Calcd for as in Example I: C,57.99; H, 2.43; N, 16.91; In, 17.32; and Cl, 5.35. Found:C, 57.53; H, 2.65; N, 16.81; In, N.D.; and Cl, 5.68.

EXAMPLE IV

Large Scale Synthesis of Chloroindium Phthalocyanine using a mixture of Dimethylaminoethanol and Chloronaphthalene as Reaction Solvent.

A 10 gallon glass-lined reactor was purged with nitrogen and charged with 24.0 kilograms of 1-chloronaphthalene and 3.35 kilograms of dimethylaminoethanol. The reactor agitator was started at 100 rpm and 1.66 kilograms of anhydrous indium chloride was charged, followed by 4.88 kilograms of ortho-phthalodinitrile. The reactor was purged with nitrogen and heating, using steam, was applied to the reactor jacket. The steam pressure was gradually increased from 100 kPa to 270 kPa in order to effect a reactor temperature increase to 135° C. over about 30 minutes. A small exotherm occurred with the reactor temperature increasing to 142° C. The reaction was continued at this temperature for 30 minutes, after which 650 kPa steam was applied to increase the reactor temperature to about 166° to 168° C. The reaction was continued for an additional 1.5 hours at this temperature, after which cooling was applied to cool the reactor to 55° C. over about 30 minutes under nitrogen purge. The reactor contents were discharged into an agitated vacuum filter and the filtrate drained. The pigment was reslurry washed with 25 kilograms of methanol used to rinse the reactor and then four times with 25 kilograms of isopropanol at room temperature. The wet cake was reslurry washed four times with 25 kilograms of dimethylformamide at about 70° to 75° C., four times with 25 kilograms of deionized water at about 70° to 75° C. and once with 25 kilograms of methanol at room temperature. The pigment was dried in a vacuum shelf drier at about 60° to 70° C. The desired chloroindium phthalocyanine product was isolated as 3.99 kilograms of a blue pigment, in 80.2 percent yield based on the starting indium chloride. The UV-Vis spectra of a dilute solution of the pigment in chloronaphthalene, FTIR spectra, and the XRD pattern confirmed that the desired product was obtained and confirmed that no metal free phthalocyanine was present.

The synthesis of chloroindium phthalocyanine using a mixture of dimethylaminoethanol and chloronaphthalene as the reaction solvent was repeated as above in another 10 gallon scale experiment resulting in 4.29 kilograms of pigment, or 86.2 percent yield based on the starting indium chloride.

COMPARATIVE EXAMPLE I

Synthesis of Chloroindium Phthalocyanine using Quinoline as Reaction Solvent.

Ortho-phthalodinitrile (64.0 grams) was added to 320 grams of quinoline in a 1,000 mL, three necked round bottom flask. Anhydrous indium trichloride (22.1 grams) was added under agitation. The reaction mixture was heated to 160° to 165° C. and the reaction continued for 5 hours. After cooling to about 50° C. under nitrogen atmosphere, the pigment was filtered, using vacuum filtration with a Buchner funnel. The wet cake was washed in the funnel with 300 grams methanol and then reslurried and washed successively with: 300 grams dimethylformamide (two times at 70° C.), 300 grams of methanol at room temperature, 300 grams dimethylformamide at 70° C., 300 grams deionized water at 70° C., and 300 grams of methanol (two times at room temperature), and dried. The desired chloroindium phthalocyanine product was isolated as 28.5 grams of a blue pigment, in 43.0 percent yield based on the starting indium chloride. The UV-Vis spectra of a dilute solution of the pigment in chloronaphthalene confirmed that the desired product was obtained and confirmed that no metal free phthalocyanine was present.

COMPARATIVE EXAMPLE II

Synthesis of Chloroindium Phthalocyanine using Chloronaphthalene as Reaction Solvent.

The reaction of Comparative Example I was repeated with the exception that chloronaphthalene was used as the reaction solvent. The reaction mixture was heated to 163° to 173° C. and continued for 3 hours. After cooling to about 55° C. over about 30 minutes under nitrogen atmosphere, the pigment was filtered, using vacuum filtration with a Buchner funnel. The wet cake was washed in the funnel with 300 grams methanol and then reslurried and washed successively with: 300 grams dimethylformamide (three times at 70° C.), 300 grams deionized water (five times at 70° C.), 300 grams of methanol (two times at room temperature), and dried. The desired chloroindium phthalocyanine product was isolated as 21.7 grams of a blue pigment, in 32.7 percent yield based on the starting indium chloride. The UV-Vis spectra of a dilute solution of the pigment product in chloronaphthalene showed that the desired product was contaminated with a minor amount of at least 5 percent by weight of metal-free phthalocyanine.

COMPARATIVE EXAMPLE III

Synthesis of Chloroindium Phthalocyanine using N-methylpyrrolidone as Reaction Solvent.

The reaction of Comparative Example I was repeated with the exception that N-methylpyrrolidone was used as reaction solvent. The reaction mixture was heated to 165° to 172° C. and the reaction continued for 3 hours. After cooling to about 50° C. in about 45 minutes under nitrogen atmosphere, the pigment was filtered, using vacuum filtration with a Buchner funnel. The wet cake was washed in the funnel with 160 grams methanol and then reslurried and washed successively with: 150 grams dimethylformamide (three times at 70° C.), 150 grams deionized water (two times at 70° C.), 150 grams of methanol (two times at room temperature), and dried. The desired chloroindium phthalocyanine product was isolated as 9.75 grams of a blue pigment, in 14.7 percent yield based on the starting indium chloride. The UV-Vis spectra of a dilute solution of the pigment in chloronaphthalene confirmed that the desired product was obtained and confirmed that no metal free phthalocyanine was present.

COMPARATIVE EXAMPLE IV

Large Scale Synthesis of Chloroindium Phthalocyanine using Quinoline as Reaction Solvent.

A 10 gallon glass-lined reactor was purged with nitrogen and charged with 17.6 kilograms of quinoline. The reactor agitator was started at 100 rpm and 1.2 kilograms of anhydrous indium chloride and 3.44 kilograms of ortho-phthalodinitrile were charged. The reactor was purged with nitrogen and heating, using steam, was applied to the reactor jacket. The steam pressure was gradually increased from 100 kPa to 600 to 650 kPa in order to effect a reactor temperature increase to 164° to 166° C. in about 60 minutes. The reaction was continued at this temperature for eight hours, after which cooling was applied and the reactor cooled to 60° C. in about 20 minutes under nitrogen purge. The reactor contents were discharged into an agitated vacuum filter and the filtrate drained. The pigment was reslurry washed with 12 kilograms of methanol used to rinse the reactor and then two times with 16 kilograms of dimethylformamide at about 70° to 75° C., and with 15 kilograms of methanol at about 55° C. The wet cake was again reslurry washed with 16 kilograms of dimethylformamide at about 70° to 75° C., and with 15 kilograms of methanol at about 55° C. The pigment was dried in a vacuum shelf drier at about 60° C. The desired chloroindium phthalocyanine product was isolated as 1.24 kilograms of a blue pigment, in 34.5 percent yield based on the starting indium chloride. The UV-Vis spectra of a dilute solution of the pigment in chloronaphthalene, FTIR spectra, and the XRD pattern confirmed that the desired product was obtained and confirmed that no metal free phthalocyanine was present.

The synthesis of chloroindium phthalocyanine using quinoline as the reaction solvent was repeated using an excess (15 mole percent) of indium trichloride in another 10 gallon scale experiment resulting in 1.5 kilograms of pigment, or 43.7 percent yield based on the starting ortha-phthalodinitrile.

Table 1 shows the influence of the solvent choice on the yield of chloroindium phthalocyanine. Using dimethylaminoethanol and especially the mixed chloronaphthalene/dimethylaminoethanol solvent system, the isolated yield of the desired CIInPc product was significantly improved.

TABLE 2

Isolated Yields of Chloroindium Phthalocyanine as function of dimethylaminoethanol/ortho-phthalodinitrile molar ratio.

| EXAMPLE | SOLVENT SYSTEM | DIMETHYLAMINOETHANOL/ o-PHTHALODINITRILE MOLAR RATIO | YIELD % |
|---|---|---|---|
| II | Chloronaphthalene/Dimethylaminoethanol | 1:1 | 81.5 |
| Repeat of II | Chloronaphthalene/Dimethylaminoethanol | 1:1 | 85.0 |
| Modification of II | Chloronaphthalene/Dimethylaminoethanol | 0.5:1 | 60.4 |
| Modification of II | Chloronaphthalene/Dimethylaminoethanol | 0.25:1 | 25.7 |

Table 2 shows the influence of the ratio of dimethylaminoethanol/ortho-phthalodinitrile on the yield of chloroindium phthalocyanine when using the mixed chloronaphthalene/dimethylaminoethanol solvent system. A 1:1 molar ratio of dimethylaminoethanol/ortho-phthalodinitrile is sufficient to obtain the desired high yields.

TABLE 3

Comparative Results for Large Scale Batches

| Example | Scale (kg) | Yield (Percent) | Solvent |
|---|---|---|---|
| Comparative Example IV | 1.24 | 34.5 | Quinoline |
| Repeat of Comparative Example IV | 1.50 | 43.7 | Quinoline |
| IV | 3.99 | 80.2 | Chloronaphthalene/ DMAE |
| Repeat of IV | 4.29 | 86.2 | Chloronaphthalene/ DMAE |

Table 3 shows the significantly higher yields obtained in the large scale experiments when using the chloronaphthalene/dimethylaminoethanol solvent system compared to the use of quinoline as reaction solvent as described in the prior art.

The chloroindium phthalocyanines were evaluated as photogenerators in xerographic imaging devices which were prepared by the following procedures.

A first type of imaging device was prepared by providing an aluminized MYLAR ® substrate which was coated with a Nylon 8 solution, prepared by dissolving 5 grams of Nylon 8 (Dainippon Ink and Chemical Company) in 24 grams of n-butanol and 4 grams of water using a 1 mil gap applicator. This layer was dried at 135° C. for 20 minutes; the final thickness was measured to be 0.6 micron. A dispersion of the CIInPc was prepared by ball milling 0.35 gram of the CIInPc respectively, and poly(vinyl butyral) in 13.4 grams of butyl acetate in a 30

TABLE 1

Isolated Yields of Chloroindium Phthalocyanine as Function of Solvent Choice.

| EXAMPLE | SOLVENT | REACTION Time Hrs. | Temp. °C. | YIELD % | REMARKS |
|---|---|---|---|---|---|
| Comp Ex I | Quinoline | 5 | 170 | 43.0 | Standard procedure |
| Comp Ex II | Chloronaphthalene | 3 | 170 | 32.7 | H$_2$Pc contamination |
| Comp Ex III | N-methylpyrrolidone (NMP) | 3 | 170 | 14.7 | |
| I | Dimethylaminoethanol (DMAE) | 3 | 139 | 52.0 | DMAE reflux temp. |
| II | Chloronaphthalene/Dimethylaminoethanol | 3 | 165 | 81.5 | |
| III | N-methylpyrrolidone/Dimethylaminoethanol | 3 | 165 | 60.5 | | milliliter jar containing 70 grams of ⅛ inch stainless steel balls. The dispersion was milled for 20 hours then was coated onto the Nylon 8 layer described above using a 1 mil applicator. The thus formed photogenerating layer was dried at 100° C. for 10 minutes; its final thickness was determined to be about 0.40 micron.

Hole transporting layers solution were prepared by dissolving 5.4 grams of N,N'-diphenyl-N,N-bis(3-methyl phenyl)-1,1'-biphenyl-4,4'-diamine, 8.1 grams of polycarbonate in 52 grams of chlorobenzene. The solution was coated onto the ClInPc generator layer using an 8 mil film applicator. The charge transporting layer thus obtained was dried at 115° C. for 60 minutes to provide a final thickness of about 23 microns.

A second type of imaging device was prepared by providing a titanized MYLAR ® substrate which was coated with a silane blocking layer and a DuPont 49000 polyester adhesive layer. The photogenerating chloroindium phthalocyanine pigment was vacuum deposited thereon, in a vacuum coater, providing a charge generator layer with a thickness of 0.1 micron. A charge transport layer composed of 35% by weight N,N'-diphenyl-N,N-bis(3-methyl phenyl)-1,1'-biphenyl-4,4'-diamine and 65% by weight polycarbonate (MAKROLON ®) was then coated from a dichloromethane solution to provide a final thickness of 25 microns for the transport layer. The device was dried at 135° C. for 20 minutes in a forced air oven.

The xerographic electrical properties of a photoresponsive imaging members prepared as described above were determined by electrostatically charging the surface thereof with a corona discharge source until the surface potential, as measured by a capacitively coupled probe attached to an electrometer, attained an initial dark value, $V_0$, of $-800$ volts. After resting for 0.5 seconds in the dark, the charged member reached a surface potential, $V_{ddp}$, or dark development potential. The member was then exposed to filtered light from a Xenon lamp. A reduction in surface potential from $V_{ddp}$ to a background potential, $V_{bg}$, due to the photodischarge effect, was observed. The dark decay in volts per second was calculated as $(V0-V_{ddp})/0.5$. The percent of photodischarge was calculated as $100\times(V_{ddp}-V_{bg})/V_{ddp}$. The half-exposure energy, $E_{\frac{1}{2}}$, the required exposure energy causing reduction of the $V_{ddp}$ to half of its initial value, was determined. The wavelength of light selected for our measurements was 800 nanometers.

The disclosure of all aforementioned patents, and publications are totally incorporated by reference herein.

Other modifications of the present invention may occur to those skilled in the art based upon a review of the present application and these modifications, including equivalents thereof, are intended to be included within the scope of the present invention.

What is claimed is:

1. A process for the preparation of chloroindium phthalocyanine which consists essentially of heating a mixture of indium trichloride and ortho-phthalodinitrile in a mixture of solvents of a dialkylaminoalkanol and a high boiling second solvent; and cooling the mixture to enable precipitation.

2. A process according to claim 1 wherein said high boiling second solvent is a halogenated hydrocarbon.

3. A process according to claim 2 wherein said halogenated hydrocarbon is 1-chloronaphthalene.

4. A process according to claim 1 wherein said dialkylaminoalkanol is dimethylaminoethanol.

5. A process according to claim 1 wherein said dialkylaminoalkanol is dimethylaminoethanol and said high boiling second solvent is 1-chloronaphthalene.

6. A process according to claim 1 wherein the orthaphthalodinitrile to dialkylaminoalkanol solvent molar ratio is about 1:1.

7. A process according to claim 4 wherein the phthalodinitrile to dimethylaminoethanol solvent molar ratio is at least about 1:1 to about 1:5.

8. A process according to claim 1 wherein the indium trichloride to ortho-phthalodinitrile molar ratio is from about 1:4 to about 1:6.

9. A process according to claim 5 wherein the solvent mixture of dimethylaminoethanol and 1-chloronaphthalene is in a weight ratio of about 1:6 to about 1:20.

10. A process according to claim 5 wherein the orthaphthalodinitrile is dissolved in a solvent mixture of dimethylaminoethanol and chloronaphthalene and wherein the nitrile to solvent weight ratio is of from about a 1:4 to about 1:10.

11. A process according to claim 1 wherein the dialkylaminoalkanol solvent is selected from the group consisting of dimethylaminoethanol, dimethylaminopropanol isomers, diethylaminoethanol, and diethylaminopropanol isomers.

12. A process according to claim 1 wherein the high boiling second solvent is selected from the group of halogenated aromatic hydrocarbons and N-alkylpyrrolidones.

13. A process according to claim 1 wherein the high boiling second solvent is selected from the group consisting of chloronaphthalenes, chlorobenzenes, and chlorotoluenes.

14. A process according to claim 1 wherein the high boiling second solvent is selected from the group consisting of N-methyl pyrrolidone, N-ethylpyrrolidone, and N-cyclohexylpyrrolidone.

15. A process according to claim 5 wherein there is obtained a chloroindium phthalocyanine product corresponding to the $\beta$-polymorph.

16. A process according to claim 1 wherein heating is accomplished from about 125° C. to about 250° C.

17. A process according to claim 1 wherein cooling is accomplished by lowering the temperature of the reaction mixture to from about 90 to about 0° C. over a period of about 0.5 to about 2.0 hours.

18. A process according to claim 16 wherein heating is accomplished by heating the reaction mixture to about the boiling temperature of the dialkylaminoalkanol solvent and then heating to from about 160° C. to about 250° C. to complete the reaction.

19. A process according to claim 5 wherein heating is accomplished over about 0.5 hours to about 10 hours at about 133° to 135° C. and then heating to about 160° C. to about 200° C. to complete the reaction.

20. A process according to claim 18 wherein heating is accomplished by heating first to about the boiling temperature of the dialkylaminoalkanol solvent for about 0.1 hours to 2 hours, and then increasing heating temperature to about 160° C. to about 250° C. for about 0.5 hours to 10 hours to complete the reaction.

21. A process according to claim 18 wherein the dialkylaminoalkanol solvent is dimethylaminoethanol and the high boiling second solvent is 1-chloronaphthalene in a weight ratio of from about 1:1 to about 1:50.

22. A process according to claim 20 wherein heating is accomplished in a mixture of solvents of dimethylaminoethanol and 1-chloronaphthalene at about 133° to 135° C. for about 0.1 hours to 2 hours, and then heating to about 160° C. to about 200° C. for about 0.5 hours to about 10 hours to complete the reaction.

23. A process for the preparation of metal phthalocyanines which consists essentially of heating a mixture of a metal halide and phthalodinitrile in a mixture of solvents of a dialkylaminoalkanol and a high boiling second solvent; and cooling the mixture to enable precipitation.

24. A process according to claim 23 wherein the metal halide is selected from the group of indium chloride, gallium chloride, aluminum chloride, vanadium chloride, germanium chloride, and titanium chlorides.

25. A process according to claim 23 including separating the desired metal phthalocyanine from the solution followed by washing.

26. A process according to claim 1 further comprising separating the chloroindium phthalocyanine product from the mixture followed by an optional washing.

27. A process according to claim 1 wherein said dialkylaminoalkanol has alkyl groups containing 1 to 12 carbon atoms.

28. A process for the preparation of haloindium phthalocyanine which consists essentially of heating a mixture of a indium trihalide and phthalodinitrile in a mixture of solvents of a dialkylaminoalkanol and a high boiling second solvent; and cooling the mixture to enable precipitation of the haloindium phthalocyanine product.

29. A process according to claim 28 including separating the haloindium phthalocyanine product from the mixture followed by washing.

30. A process according to claim 29 wherein the indium trihalide is selected from the group consisting of chloro-, bromo-, iodo-, and fluro-indium salts.

* * * * *